United States Patent [19]

Charm et al.

[11] 4,043,759

[45] Aug. 23, 1977

[54] METHOD OF DETERMINING METHOTREXATE

[76] Inventors: Stanley E. Charm; Henry E. Blair, both of 136 Harrison Ave., Boston, Mass. 02111

[21] Appl. No.: 650,690

[22] Filed: Jan. 20, 1976

[51] Int. Cl.² ............ G01N 33/16; G01N 31/06; A61K 43/00
[52] U.S. Cl. ............... 23/230.6; 23/230 B; 195/103.5 R; 424/1
[58] Field of Search ............ 23/230 B, 230.6; 195/103.5 R; 424/1

[56] References Cited

U.S. PATENT DOCUMENTS 3,981,983  9/1976  Caston ............... 23/230 B X

OTHER PUBLICATIONS

C. E. Myers et al., Proc. Nat. Acad. Sci. USA, 72 (9), 3683–3686, (Sept. 1975).
D. S. Skelly et al., Clinical Chem., 19(2), 146, 147, 148, 150, 157, 158 (1973).
B. Overdijk et al., Clin. Chim. Acta, 59(2), 177–182 (1975).
Chemical Abstracts, 82:92829w (1975).
Chemical Abstracts, 82:106098w (1975).

Primary Examiner—Sidney Marantz
Attorney, Agent, or Firm—Richard P. Crowley

[57] ABSTRACT

A radioassay system for the determination of methotrexate in biological fluids based on the competitive binding of labeled and unlabeled methotrexate to the enzyme dihydrofolate reductase. Samples of unknown methotrexate level are mixed with $I^{125}$ labeled methotrexate. A portion of the total methotrexate present is bound by the addition of enzyme, and the unbound methotrexate is removed with charcoal. The level of bound $I^{125}$ labeled methotrexate is measured in a gamma ray counter. To calculate the methotrexate level of the unknown samples, the displacement of bound labeled methotrexate caused by the unknowns is compared to the displacement caused by known methotrexate standards.

17 Claims, 1 Drawing Figure

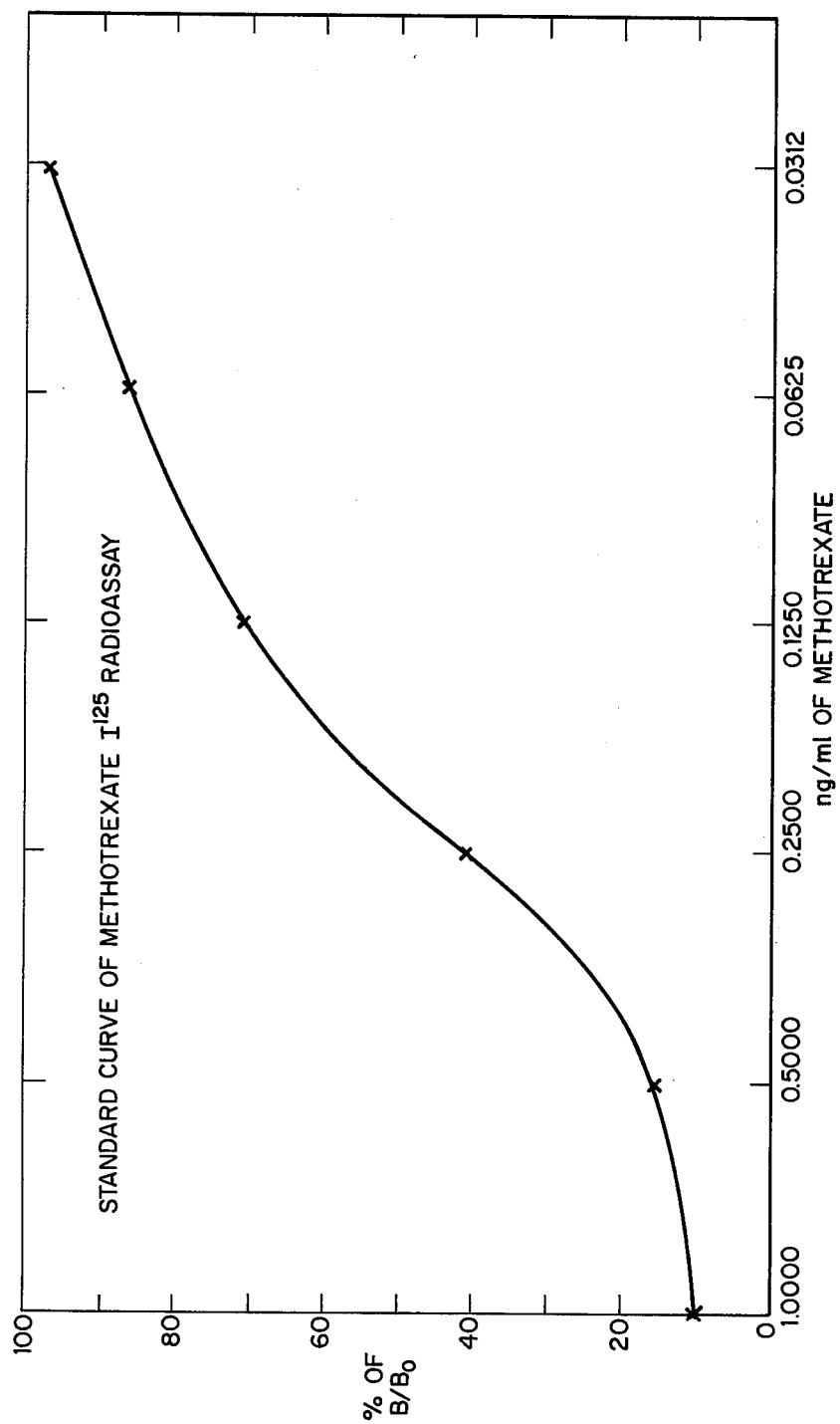

METHOD OF DETERMINING METHOTREXATE

BACKGROUND OF THE INVENTION

Methotrexate is an antineoplastic and immunosuppressive agent useful, for example, in the chemotherapy treatment of leukemic meningitis, osteogenic sarcoma, psoriasis and other disorders and malignancies in animals and man. Methotrexate is an antagonist to folic acid.

The drug methotrexate competitively inhibits the enzyme dihydrofolate reductase. The conversion of dihydrofolate to tetrahydrofolate is necessary for the biosynthesis of thymidylic acid, a precursor of DNA. Inhibition of dihydrofolate reductase by methotrexate blocks the DNA synthetic pathway and is selectively lethal to rapidly dividing cells.

The use of methotrexate in systemic and intrathecal, as well as conventional and high-dose drugs, therapy requires that the drug be carefully monitored to avoid clinical toxicity to the patient, and to permit the introduction of a rescue agent like leucovorin before the critical toxicity level is reached. Methotrexate is eliminated by the patient with time; however, the elimination rate often varies markedly in some patients. Toxicity can arise from the delayed elimination of the drug by the patient. Thus, a rapid, simple and accurate technique and system for determining the level of methotrexate is important.

Present techniques for the monitoring of methotrexate in biological fluids are not wholly satisfactory, since such techniques are often complex, time-consuming and of limited availability. Some present suggested methods to assay methotrexate levels include: an enzyme-inhibition assay; radioimmunoassay, a flurorometrical method, and the use of a tritium radiolabeled drug.

One radioassay technique (see Raso and Schreiber, *Cancer Research* 35, 1407, June 1975) employs a tritium-labeled methotrexate, and uses a human serum buffer system with an enzyme from leukemia cells in a sequential assay technique, with the enzyme added first to the methotrexate sample.

Another radioassay technique, the Myers et al system (see Myers, Lippman, Eliot and Chabner, *Proc. Nat. Acad. Sci. USA*, Vol. 72, No. 9, pp. 3683-3686, September 1975, Medical Sciences), employs a competitive protein binding assay using tritium-labeled methotrexate, and uses a heparin buffer system and plasma samples.

SUMMARY OF THE INVENTION

Our invention relates to a method and apparatus for the determination of methotrexate. In particular, our discovery concerns a competitive binding radioassay method and kit for the quantitative determination of methotrexate in biological fluids employing a methotrexate $I^{125}$ derivative.

We have discovered a radioassay method and have developed a combination of materials in kit form to determine methotrexate, particularly for the in vitro determination of methotrexate, concentration levels in biological fluids, such as, but not limited to, blood serum, plasma, cerebrospinal fluid and urine. Our method is sensitive to methotrexate levels as low as about 0.03 nanograms per milliliter (ng/ml); for example, in the 0.05 to about 1.0 ng/ml range, and will detect blood serum levels down to 0.6 ng/ml or $1.1 \times 10^{-9}$ moles/liter. The upper range limit of detection can be increased by suitable dilution or by adjusting the ratio of enzyme to the labeled methotrexate, so that, if necessary or desirable, the upper range limit of sensitivity can be increased up to a saturated methotrexate solution. In the determination of methotrexate in biological fluids, sensitivity in the range of 0.05 to 0.5 ng/ml is typically effective.

Our method is sensitive, rapid with results typically within 20 to 30 minutes, simple with easy-to-follow known laboratory procedures, and accurate with low cost. Our method is based on the competitive binding of $I^{125}$ labeled and unlabeled methotrexate to the enzyme dihydrofolate reductase. In our method, samples, such as biological fluids, containing unknown levels of methotrexate, which levels are to be determined, are mixed with a buffered solution containing known quantities of $I^{125}$ labeled methotrexate. Known quantities of competitive binding enzymes, such as a dihydrofolate reductase, are added, which competitively bind to a portion of the total labeled and unlabeled methotrexate present in the solution. Unbound methotrexate is then removed, such as by adsorption of the unbound methotrexate, with an adsorbent material, and the removal by centrifuging of the free absorbed drug and the adsorbent material, to provide a supernatant liquid essentially free of the free or unbound methotrexate.

Typically, a protein-coated particular adsorbent material, such as a dextran and/or hemoglobin-treated fine particles of charcoal, is used to remove the free drug. Although our technique and method may be used, other methods are also adaptable; for example, liquid chromatography, ion-exchange resins and ultrafiltration.

The level of the bound derivative-labeled $I^{125}$ methotrexate in the supernatant liquid is then determined, employing a means to measure the radioactivity of the $I^{125}$ in the sample, such as by a gamma ray counter. The methotrexate level of the unknown samples tested is then calculated by comparison of the displacement of the bound labeled methotrexate caused by the unknown samples to the displacement caused by known levels of methotrexate concentration standards. Typically, the determination may be made by comparison with a standard plot curve or standard data table.

The labeled methotrexate employed in our method is a $I^{125}$ isotope having a half-life of about 60.0 days. The labeled $I^{125}$ methotrexate is supplied in derivative form, with the methotrexate in a solution (the $I^{125}$ derivative compound reacted with MTX). The labeled $I^{125}$ methotrexate is supplied with the kit apparatus in an organic solvent to prevent freezing, such as in an aqueous water-soluble material, such as dimethyl formamide solution. Water can be added to the solution to obtain the desired gamma ray count.

Our radioassay kit for use in the determination of methotrexate by our method comprises a buffer solution A and a buffer solution B component for use in preparing standard data, which are admixed prior to use to provide a buffered solution of a protein. However, human plasma and serum can be employed, although it is not recommended, since there is a risk of hepatitis. Preferably, the protein employed should be a nonhuman protein serum, such as an animal serum like and preferably bovine serum. The protein solution used is buffered at about a pH of 6.2, since this is the optimum pH for binding methotrexate to the enzyme dihydrofolate reductase, although, if desired, other pH ranges may be used.

Typical solutions A and B are: Buffer A — 500 ml of distilled water — 0.15M phosphate buffer pH 6.2 with a preservative, such as 0.05% sodium azide; and Buffer B — a 10% bovine serum in Buffer A pH 6.2. The kit also includes an aqueous solution of a methotrexate standard at 100,000 ng/ml; a labeled methotrexate $I^{125}$ in 50% dimethyl formamide of approximately 2 μCi; a dextran and gelatin-coated charcoal particles; a TPNH (triphosphopyridine nucleotide) enzyme dihydrofolate reductase (prepared from L. casei by New England Enzyme Center, Boston, Massachusetts) and cotton swabs for use in the method.

Our methotrexate radioassay kit and our method for determining methotrexate will be described in their preferred embodiments for the purpose of illustration. However, it is recognized and is a part of our apparatus, kit and method and is within the spirit and scope of our invention that various changes and modifications can be and may be made by those persons skilled in the art to our apparatus and method.

BRIEF DESCRIPTION OF THE DRAWING

The drawing shows a standard semilog curve obtained by our radioassay method, relating the level of methotrexate to the ratio B/Bo, representing the ratio of the standard count (B) to the zero count (Bo) of the labeled $I^{125}$ methotrexate.

DESCRIPTION OF THE EMBODIMENTS

An aqueous solution of 1.5 M of a sodium phosphate buffer with 0.5% sodium azide in the amount of 50 ml is added to sufficiently distilled water to make 500 ml of buffered solution (Buffer A). A known amount of bovine serum (250-280 mg) Buffer B component is dissolved in 40 ml of distilled water and is added to 360 ml of Buffer A to provide a buffered bovine serum (Buffer B) for use in preparing the standard data.

A 50% water 50% dimethyl formamide solution of 2 ml of a methotrexate $I^{125}$ derivative (approximately μCi) is admixed with 8 ml of Buffer A. The solution should be light-protected and held cold while using and stored at 4° C. The solution has about 19,000 cpm/100 μl. A methotrexate standard solution is provided for use which contains a known amount of methotrexate 100,000 ng/ml which, like the labeled solution, should be stored at 4° C and be light-protected. An amount of 0.5 grams of finely divided dextran-gelatin-treated charcoal is provided and prior to use added to 50 ml of distilled water and stored at 4° C as a charcoal suspension. A known amount of enzyme dihydrofolate reductase from L. casei 0.02 units (micromoles of dihydrofolate reduced/min.), when ready to be used, is admixed in a vial with 10 ml cold Buffer A with vigorous mixing. Patient samples to be tested should be protected from light, since methotrexate in dilute solution is light-sensitive.

The preparation of methotrexate standards is by serial dilutions of the 100,000 ng/ml stock in Buffer B as follows:

a) $100{,}000 \text{ ng/ml} \xrightarrow{100\ \mu l} \dfrac{0.9\text{ ml}}{(10{,}000 \text{ ng/ml})}$ b) $10{,}000 \text{ ng/ml} \xrightarrow{100\ \mu l} \dfrac{0.9 \text{ ml}}{(1{,}000 \text{ ng/ml})}$ c) $1{,}000 \text{ ng/ml} \xrightarrow{100\ \mu l} \dfrac{0.9 \text{ ml}}{(100 \text{ ng/ml})}$ d) $100 \text{ ng/ml} \xrightarrow{100\ \mu l} \dfrac{0.9 \text{ ml}}{(10 \text{ ng/ml})}$ e) $10 \text{ ng/ml} \xrightarrow{0.6 \text{ ml}} \dfrac{5.4 \text{ ml}}{(1 \text{ ng/ml})}$ f) $1 \text{ ng/ml} \xrightarrow{3.0 \text{ ml}} \dfrac{3.0 \text{ ml}}{(0.5 \text{ ng/ml})}$ g) $0.5 \text{ ng/ml} \xrightarrow{3.0 \text{ ml}} \dfrac{3.0 \text{ ml}}{(0.25 \text{ ng/ml})}$ h) $0.25 \text{ ng/ml} \xrightarrow{3.0 \text{ ml}} \dfrac{3.0 \text{ ml}}{(0.125 \text{ ng/ml})}$ i) $0.125 \text{ ng/ml} \xrightarrow{3.0 \text{ ml}} \dfrac{3.0 \text{ ml}}{(0.0625 \text{ ng/ml})}$ j) $0.0625 \text{ ng/ml} \xrightarrow{3.0 \text{ ml}} \dfrac{3.0 \text{ ml}}{(0.031 \text{ ng/ml})}$ The preparation of patient samples, such as patient serum and spinal fluid, is as follows:

1. Take 0.3 ml of fluid to be tested and add to 2.7 ml Buffer B to provide a 1:10 dilution. If methotrexate concentration in original sample is between 0.5 and 10.0 ng/ml, it will be detected with this dilution.

2. Take 0.3 ml of 1:10 dilution and add to 2.7 ml of Buffer B to provide a 1:100 dilution. If methotrexate concentration is between 5 and 100 ng/ml, it will be detected in this dilution.

3. Take 0.3 ml of 1:100 dilution and add to 2.7 ml Buffer B to provide a 1:1000 dilution. If methotrexate concentration is between 50 and 1000 ng/ml, it will be detected in this dilution.

4. Take 0.3 ml of 1:1000 dilution and add to 2.7 ml Buffer B to provide 1:10,000 dilution. If methotrexate concentration is between 500 and 1,000 ng/ml, it will be detected in this dilution.

This dilution sequence is repeated as required.

In our method, a sample of biological fluid containing an unknown amount of methotrexate to be determined is removed from the patient and is diluted 1:10 to 1:100 or as required to permit comparison to the standard curve in a buffered animal serum solution.

The procedure to be followed for the determination of methotrexate and to obtain a standard curve of FIG. 1 is as follows:

1. Dispense duplicate 1 ml aliquots of appropriately diluted patient samples (or of each dilution if range is unknown) or methotrexate standards (where standard curve is to be prepared) into each of 2 disposable test tubes.

2. Dispense 1 ml of Buffer B into each of 4 tubes (two for a blank and two for zero concentration).

3. Accurately dispense 100 μl of methotrexate $I^{125}$ solution to each tube to obtain a count of about 16,000 to 19,000 cpm.

4. Accurately dispense 100 μl of enzyme solution to each tube except blank. Shake briefly and allow tubes to stand at least 5 minutes to provide sufficient time for the competition of the labeled $I^{125}$ and unlabeled methotrexate with the known enzyme to take place. Times of 2 to 3 minutes have been found to be too short, while over 5 minutes; e.g., 5 to 10 minutes, are preferred.

5. Add 0.2 ml of charcoal-dextran suspension to each tube (charcoal should be well suspended before adding). Shake tubes well and allow to stand 7 to 10 minutes with occasional shaking.

6. Centrifuge for 1 or 2 minutes at 2500 × g. Centrifuging collects the dextran-charcoal adsorbent on which the free drug is bonded and removes the unbonded labeled $I^{125}$ and unlabeled drug from the solution.

7. Decant supernate liquid into clean tubes. Wipe last drop with swab from tube mouth and add swab to supernate.

8. Determine radioactive count per minute in supernate liquid employing a gamma counter or other means.

The calculation for the preparation of a standard curve or the compilation of standard data and the determination of the methotrexate level of the unknown samples are based on the competition of the labeled and unlabeled methotrexate in binding the enzyme. The $I^{125}$ radioactive isotope has a half-life of 60.0 days, and thus, after assembly and preparation of the kit components, the kit should be used typically within 30 days from the birth date of the isotope $I^{125}$ used. The kit typically states on the label — storage at 4° C, and gives the expiration date of use for the labeled and unlabeled methotrexate.

The preparation of a standard curve is plotted from data obtained, employing the known serial dilution amounts of methotrexate. A standard curve as in FIG. 1 was obtained from the data of Table I and plotted as the percent of the ratio B/Bo on the ordinate to the amount of methotrexate in ng/ml on the abscissa. B/Bo is defined as the log concentration vs.

$$\frac{\text{standard count} - \text{blank}}{\text{zero count} - \text{blank}}.$$

The sample count is then converted to B/Bo; that is, $$\frac{\text{sample count}}{\text{zero count}},$$

and the results compared to the standard curve to determine the level of methotrexate in the sample. The methotrexate concentration can be calculated by multiplying the results from the standard curve (or extrapolating or interpolating the standard data) by the dilution factor, and conversion to moles/liter is made by multiplying ng/ml by $2.2 \times 10^{-9}$.

TABLE I

Methotrexate Standard Curve

| Concentration of Methotrexate (ng/ml) | Counts per Minute | $B/B_o \times 100$ |
|---|---|---|
| Blank | 1033 | — |
|  | 1268 |  |
| 0 | 6209 | 100 |
|  | 6879 |  |
| 0.031 | 6494 | 97.5 |
|  | 6327 |  |
| 0.0625 | 5699 | 86.3 |
|  | 5907 |  |
| 0.125 | 4972 | 70.7 |
|  | 4960 |  |
| 0.250 | 3297 | 42.2 |
|  | 3556 |  |
| 0.500 | 2006 | 15.1 |
|  | 1925 |  |
| 1.000 | 1705 | 10.4 |
|  | 1715 |  |

Table II shows an example of the determination of methotrexate concentration in patients's serum as determined by our method as a function of time from injection of the methotrexate into the patient.

TABLE II

Example of Methotrexate Concentration in Patient Serum as Function of Time

| Time after Injection | Dilution Factor | Counts per Minute | $B/B_o \times 100$ | Concentration of Methotrexate (ng/ml) |
|---|---|---|---|---|
| After infusion | $10^6$ | 4706 | 82.25 | $6.6 \times 10^4$ |
|  |  | 4861 |  |  |
| 24 hours | $10^5$ | 4748 | 78.3 | $7.2 \times 10^3$ |
|  |  | 4555 |  |  |
| 48 hours | $10^3$ | 2581 | 25.7 | 420 |
|  |  | 2446 |  |  |
| 63 hours | $10^3$ | 2890 | 36.2 | 290 |
|  |  | 3000 |  |  |
| 72 hours | $10^3$ | 3690 | 50.0 | 200 |
|  |  | 4002 |  |  |

Table III shows an example of the percent recovery of methotrexate by our method when added to cerebrospinal fluid, with the amount added being 100 ng/ml (0.1 ml to 0.9 ml spinal fluid).

TABLE III

| Dilution Factor | Concentration Expected (ng/ml) | cpm | $B/B_o \times 100$ | Concentration Recovery | % Recovery |
|---|---|---|---|---|---|
| 100 | 1.0 | 1759 | 11.9 | 0.95 | 95 |
|  |  | 1826 |  |  |  |
| 200 | 0.5 | 2602 | 27.1 | 0.38 | 76 |
|  |  | 2620 |  |  |  |
| 1000 | 0.1 | 5399 | 78.0 | 0.093 | 93 |
|  |  | 5282 |  |  |  |

Our method and radioassay kit for the determination of methotrexate in biological fluids permit the rapid determination of methotrexate levels with a concise, easy-to-follow lab procedure, and avoid many of the difficulties and disadvantages associated with past methods of methotrexate determination.

What is claimed is:

1. A method for the quantitative determination of methotrexate in a sample containing at least about 0.03 nanograms per milliliter of free methotrexate, which method comprises:
   a. mixing a known amount of the enzyme dihydrofolate reductase and a known amount of $I^{125}$ labeled methotrexate to the sample and allowing the mixture to stand for a period of at least about 5 minutes to permit the competitive binding of the sample and labeled methotrexate;
   b. removing free unbound methotrexate;
   c. measuring the gamma ray count of the $I^{125}$ labeled bound methotrexate in the remaining sample which is essentially free of unbound methotrexate; and
   d. determining the amount of methotrexate in the sample by comparison of the measured gamma ray count with standard quantitative data.

2. The method of claim 1 wherein the methotrexate is diluted by an aqueous buffered solution, and the amount of methotrexate in the diluted sample ranges from about 0.05 to 1.0 nanograms per milliliter.

3. The method of claim 1 wherein the free unbound methotrexate is removed by the addition of a protein-treated sorbent material which preferentially adsorbs free methotrexate, and the removal of such sorbent material with the free unbound methotrexate.

4. The method of claim 3 wherein the sorbent material is a gelatin-, dextran- or hemoglobin-treated charcoal particulate material.

5. The method of claim 1 wherein the sample is a biological fluid of blood serum, spinal fluid or urine.

6. The method of claim 1 wherein the competitive binding of the methotrexate of the sample and the labeled $I^{125}$ methotrexate in the presence of the enzyme is carried out in an aqueous buffered solution at a pH of about 6.2.

7. The method of claim 1 wherein the amount of methotrexate is determined by converting the measured gamma ray count to a ratio B/Bo of the sample count B to a zero blank Bo, and comparing the ratio to a standard table or curve of B/Bo to a known level of methotrexate.

8. The method of claim 1 wherein the sample is a biological fluid removed from a patient, and which includes making a dilution of the sample in a buffered aqueous solution of a pH of about 6.2 to cover the suspected level of methotrexate in the sample in the range of 0.05 to 0.5 ng/ml.

9. The method of claim 1 which includes preparing a series of dilutions of a known amount of methotrexate in an aqueous buffered solution of about 6.2, the dilutions being sufficient to cover the range of the suspected methotrexate in the sample, treating such known dilutions in the same manner as the sample, and preparing a standard data table or curve from such dilutions.

10. The method of claim 1 wherein the determination is carried out in an aqueous buffered solution of a non-human serum.

11. The method of claim 1 wherein the enzyme dihydrofolate is derived from *L. casei*.

12. The method of claim 1 wherein the determination is carried out in an aqueous, phosphate-buffered solution at a pH of about 6.2 of a bovine serum.

13. The method of claim 1 wherein the enzyme is TPNH dihydrofolate reductase.

14. The method of claim 1 wherein the labeled $I^{125}$ methotrexate is in aqueous, water-soluble, organic, solvent solutions.

15. The method of claim 15 wherein the organic solvent is dimethyl formamide.

16. A method for the quantitative determination of methotrexate in a biological fluid sample which contains at least about 0.03 nanograms per milliliter of free methotrexate, which method comprises:

a. admixing a known quantity of the enzyme TPNH dihydrofolate reductase and a $I^{125}$ methotrexate derivative in an aqueous buffered diluted solution of the sample at a pH of about 6.2 and allowing the admixture to stand for a predetermined period of time of at least 5 minutes to permit the competitive binding of the methotrexate of the sample and the $I^{125}$ labeled methotrexate with the enzyme, the sample diluted to cover the range of methotrexate in the sample of from about 0.05 to 1.0 ng/ml;

b. adding a sorbent material which preferentially binds the unbound methotrexate from the biological sample and the unbound $I^{125}$ methotrexate thereon;

c. removing the sorbent material with the unbound methotrexate to provide a solution essentially free of unbound methotrexate;

d. measuring the gamma ray count of the sample solution; and e. calculating the amount of methotrexate in the sample by comparison of the gamma ray count with standard data of gamma ray count with known amounts of methotrexate.

17. A method for the quantitative determination of methotrexate in a biological fluid, which method comprises:

a. radioisotopically relating the bound amounts of an $I^{125}$ methotrexate derivative and known concentrations of methotrexate in a first system containing
 i. a predetermined amount of $I^{125}$ methotrexate derivative,
 ii. a predetermined amount of unlabeled methotrexate, and
 iii. TPNH dihydrofolate reductase which competitively binds to the methotrexate;

b. radioisotopically determining the bound amount of said $I^{125}$ labeled methotrexate derivative in a second system containing
 i. said predetermined amount of $I^{125}$ methotrexate derivative,
 ii. said TPNH dihydrofolate reductase, and
 iii. a test sample of the biological fluid to be determined; and c. correlating the bound amount of $I^{125}$ labeled methotrexate derivative determined in step (b) through the relationship determined in step (a) to determine the concentration of methotrexate in the test sample.

* * * * *